United States Patent [19]

Buendia et al.

[11] 4,109,009
[45] Aug. 22, 1978

[54] ANALGESIC, RELAXANT, AND ANTI-INFLAMMATORY CYCLOPENTANOL DERIVATIVES

[75] Inventors: Jean Buendia, Nogent-sur-Marne; Jeanine Schalbar, Suresnes, both of France

[73] Assignee: Roussel Uclaf, Paris, France

[21] Appl. No.: 717,048

[22] Filed: Aug. 24, 1976

[30] Foreign Application Priority Data

Aug. 29, 1975 [FR] France ................ 75 26616

[51] Int. Cl.$^2$ .............. A61K 31/045; A61K 31/35; C07D 309/22; C07D 309/06
[52] U.S. Cl. ................ 424/283; 260/345.7 R; 260/345.7 P; 260/345.8 R; 260/345.8 P; 260/514 D; 260/514 K; 260/586 R; 424/305; 424/317; 424/331; 542/429; 560/122
[58] Field of Search ............ 260/240 R, 345.8 P, 260/345.9, 345.8, 345.7, 514 D, 514 K, 586 R; 542/429; 560/122; 424/283, 305, 317, 331

[56] References Cited

U.S. PATENT DOCUMENTS

| | | | |
|---|---|---|---|
| 3,806,535 | 4/1974 | Sakai et al. | 260/345.9 X |
| 3,839,430 | 10/1974 | Leeming et al. | 260/345.8 P X |
| 3,867,377 | 2/1975 | Kluge et al. | 260/240 R |
| 3,868,402 | 2/1975 | Martel et al. | 260/514 D X |
| 3,931,297 | 1/1976 | Crabbe | 260/240 R X |
| 3,984,459 | 10/1976 | Babej et al. | 260/240 R X |

OTHER PUBLICATIONS

Caton et al. "Prostaglandins II . . . "in Tetrahedron Ltrs. 32, pp. 3341-3344, 1972.
Hamon, A. "Synthesis of Prostanoic Acid" in Tetrahedron Ltrs. No. 50, pp. 4482, 4481, 1975, Sep. 1.

*Primary Examiner*—Winston A. Douglas
*Assistant Examiner*—Thomas A. Waltz
*Attorney, Agent, or Firm*—Hammond & Littell

[57] ABSTRACT

Novel cyclopentanol compounds of the formula

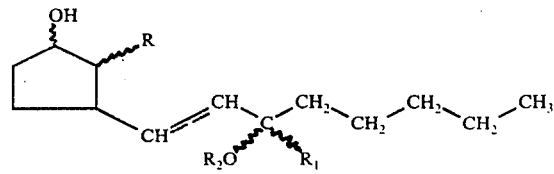

wherein R is selected from the group consisting of

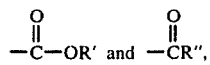

R' is selected from the group consisting of hydrogen, alkyl of 1 to 12 carbon atoms and a non-toxic, pharmaceutically acceptable cation, R" is alkyl of 1 to 6 carbon atoms, $R_1$ is selected from the group consisting of hydrogen and straight or branched chain, saturated and unsaturated alkyl of 1 to 4 carbon atoms and $R_2$ is selected from the group consisting of hydrogen and tetrahydropyranyl, the wavy lines connecting R and —OH to the cyclopentane ring and —OR$_2$ and $R_1$ to the chain indicates that the substituents may be in either of the possible positions on the carbon atom to which they are attached and the dotted line indicates the optional presence of a double bond which possess analgesic, anti-inflammatory and smooth muscle relaxant activity and their preparation.

19 Claims, No Drawings

ANALGESIC, RELAXANT, AND ANTI-INFLAMMATORY CYCLOPENTANOL DERIVATIVES

OBJECTS OF THE INVENTION

It is an object of the invention to provide the novel cyclopentanol derivatives of formula I and to provide novel processes for their preparation.

It is another object of the invention to provide novel analgesic and anti-inflammatory compositions and to provide a method of relieving pain and inflammation in warm-blooded animals.

It is a further object of the invention to provide novel smooth muscle relaxant compositions and to provide a method of relaxing smooth muscles in warm-blooded animals.

These and other objects and advantages of the invention will become obvious from the following detailed description.

THE INVENTION

The novel cyclopentanol compounds of the invention have the formula

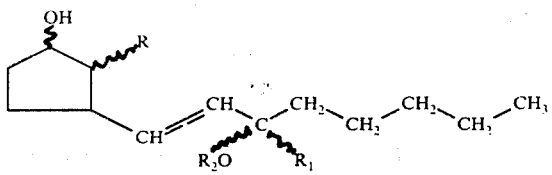

wherein R is selected from the group consisting of

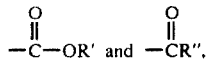

R' is selected from the group consisting of hydrogen, alkyl of 1 to 12 carbon atoms and a non-toxic, pharmaceutically acceptable cation, R" is alkyl of 1 to 6 carbon atoms, $R_1$ is selected from the group consisting of hydrogen and straight or branched chain, saturated and unsaturated alkyl of 1 to 4 carbon atoms and $R_2$ is selected from the group consisting of hydrogen and tetrahydropyranyl, the wavy lines connecting R and —OH to the cyclopentane ring and —OR and $R_1$ to the chain indicates that the substituents may be in either of the possible positions on the carbon atom to which they are attached and the dotted line indicates the optional presence of a double bond.

Among examples of the compounds of formula I, R may be —COOH or the salts thereof such as the alkali metal and alkaline earth metal salts like sodium, potassium, lithium or calcium, the magnesium salt, the ammonium salt or a salt with an organic amine or the esters thereof such as methoxycarbonyl, ethoxycarbonyl, propoxycarbonyl, isopropoxycarbonyl, butoxycarbonyl, isobutoxycarbonyl, tert.-butoxycarbonyl, pentyloxycarbonyl, hexyloxycarbonyl, decyloxycarbonyl or dodecycloxycarbonyl. Examples of R as

are methylcarbonyl, ethylcarbonyl, propylcarbonyl, butylcarbonyl and hexylcarbonyl. Examples of $R_1$ are hydrogen, methyl, ethyl, propyl, isopropyl, butyl, isobutyl, tert.-butyl, vinyl, propenyl, butenyl, ethynyl and propargyl.

Among the preferred compounds of formula I are those where R is —COOH, its alkali metal salts or its alkyl esters with 1 to 10 carbon atoms or

where R" is alkyl of 1 to 3 carbon atoms and $R_2$ is hydrogen, methyl or ethynyl. A particularly preferred group of compounds of formula I are those wherein R is alkoxycarbonyl of 1 to 3 alkoxy carbon atoms and $R_1$ is hydrogen, methyl or ethynyl.

Specific preferred compounds of formula I are the following compounds:

ethyl (1RS, 2RS, 5RS, 3'ξ) (1'E) 2,3'-dihydroxy-5-(3'-methyl-1'-octenyl)-cyclopentanecarboxylate, ethyl (1RS, 2SR, 5RS, 3'ξ) (1'E) 2,3'-dihydroxy-5-(3'-methyl-1'-octenyl)-cyclopentanecarboxylate, methyl (1RS, 2SR, 5RS, 3'SR) (1'E) 2-hydroxy-5-(3'-α-tetrahydropyranyloxy-1'-octenyl)-cyclopentanecarboxylate, ethyl (1RS, 2RS, 5RS, 3'SR) (1'E) 2hydroxy-5-(3'-hydroxy-1'-octenyl)-cyclopentanecarboxylate, ethyl (1RS, 2SR, 5RS, 3'SR) (1'E) 2-hydroxy-5-(3'-α-tetrahydropyranyloxy-1'-octenyl)-cyclopentanecarboxylate, ethyl (1RS, 2RS, 5RS, 3'SR) (1'E) 2-hydroxy-5-(3'-α-tetrahydropyranyloxy-1'-octenyl)-cyclopentanecarboxylate, ethyl (1RS, 2SR, 5RS, 3'SR) (1'E) 2-hydroxy-5-(3'-hydroxy-3'-ethynyl-1'-octenyl)-cyclopentanecarboxylate and ethyl (1RS, 2RS, 5RS, 3'SR) (1'E) 2-hydroxy-5-(3'-α-tetrahydropyranyloxy-3'-ethynyl-1'-octenyl)-cyclopentanecarboxylate.

The novel process of the invention to prepare the compounds of formula I comprises reacting a compound of the formula

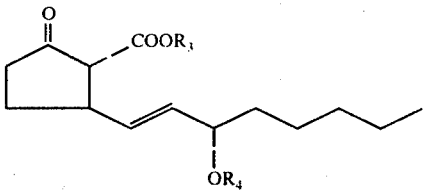

wherein $R_3$ is alkyl of 1 to 12 carbon atoms and $R_4$ is selected from the group consisting of hydrogen and 2-tetrahydropyranyl with an alkali metal hydride under mild conditions to obtain a compound of the formula

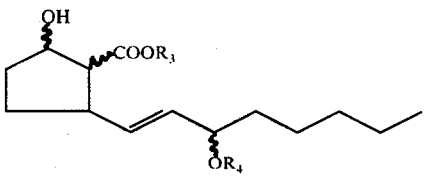

and, if desired, either reacting a compound of formula Ia with hydrogen in the presence of a catalyst to obtain a compound of the formula

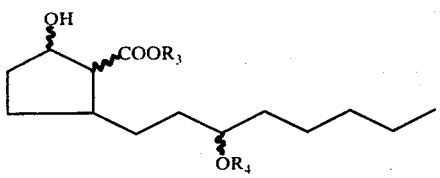
Ib or reacting a compound of formula Ia with an alkaline base and then an acid to obtain a compound of the formula

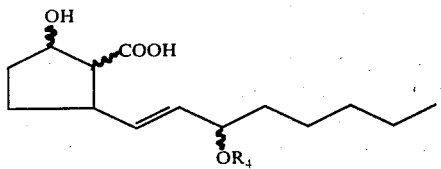
Ic which may be esterified or salified by known methods or may be reacted with an alkyl lithium of 1 to 6 carbon atoms to obtain a compound of the formula

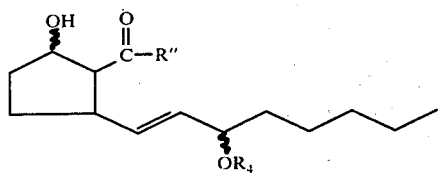
Id or reacting the compound of formula Ia wherein $R_4$ is hydrogen with an oxidizing agent to obtain a compound of the formula

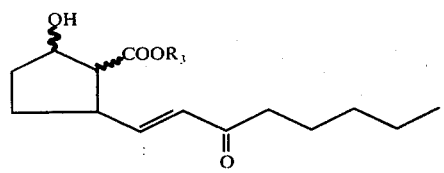
III and reacting the latter with a compound of the formula

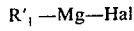
IV wherein Hal is halogen and $R'_1$ is branched or straight chain, saturated or unsaturated alkyl to obtain a compound of the formula

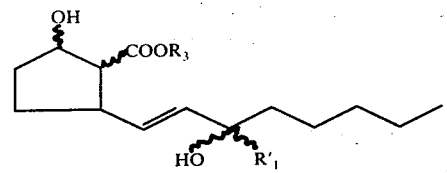
Ie

The compounds of formula II wherein $R_4$ is hydrogen may be reacted with diazomethane to obtain a compound of the formula

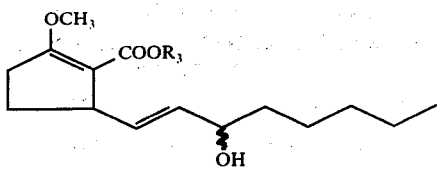
V which is then reacted with an oxidation agent to obtain a compound of the formula

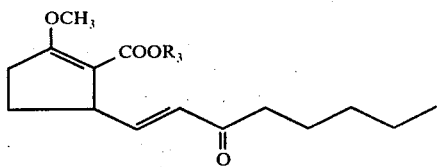
Va and the latter is reacted with a compound of formula IV to obtain a compound of the formula

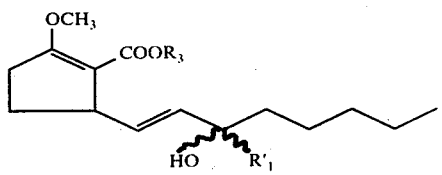
VI which is then treated with an acid to obtain a compound of the formula

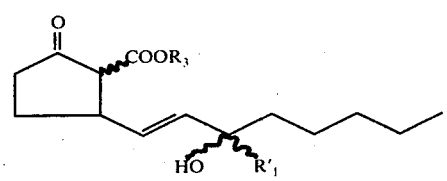
VII which may be either treated with a reducing agent under mild conditions to form a compound of formula Ie or reacted with 2,3-dihydropyran and then with a reducing agent under mild conditions to obtain a compound of the formula If The compounds Ia, Ib, Ie and If may further be treated with an alkaline base and then an acid to form the corresponding free carboxylic acids which are optionally salified or esterified by known methods.

In a preferred mode of the process of the invention, the reducing agent for treatment of a compound of formula II is an alkali metal borohydride such as sodium or potassium borohydride used in the cold but it may also be other alkali metal hydrides such as lithium aluminum hydride used at a temperature below 0° C. The catalyst for the reduction of the double bond of the compound of formula Ia is preferably palladized carbon but other catalysts such as platinum or platinum salts may be used.

The base used to treat a compound of formula Ia is preferably sodium hydroxide but may be other bases such as potassium hydroxide or alkali metal carbonates and bicarbonates such as sodium bicarbonate or potassium bicarbonate. The oxidizing agent for reaction with the compound of formula Ia when $R_4$ is hydrogen is preferably dichlorodicyanoquinone but equally useful is silver silicate under mild conditions.

The reaction of compounds of formulae III or Va with organo metallic halide of formula IV is effected under the usual conditions for this reaction and is effected in an anhydrous medium such as an aprotic solvent like ether or tetrahydrofuran. The oxidation of the compound of formula V is preferably effected with silver silicate but may be also effected with dichlorodicyanoquinone.

The acid used to treat a compound of formula VI is preferably aqueous hydrochloric acid but other acids such as sulfuric acid or aqueous trifluoroacetic acid are also useful. The reducing agent for treating the compound of formula VII and for obtaining the compound of formula If is preferably sodium borohydride used at room temperature but sodium aluminum hydride at a temperature below 0° C is also useful. The alkaline base for treatment of compounds of formula I is preferably sodium hydroxide or potassium hydroxide but equally useful are barium hydroxide, lithium hydroxide or sodium or potassium bicarbonate and to obtain the esters the corresponding alcohol is reacted with the acid in the presence of an acid agent to obtain the desired ester. The esters obtained in the process of the invention may be also transesterified with the appropriate alcohol.

The compounds of formula I wherein R' is hydrogen may be salified by known methods such as reacting the free acid with a mineral base such as sodium or potassium hydroxide or an organic base such as triethylamine. The reaction is preferably effected in at least one solvent such as water, ether, ethanol or acetone.

The compounds of formula I occur in diverse configurations with respect to the carbon atoms to which the substituents are attached and the mixtures of the compounds formed in each instance may be separated by the known physical methods, particularly chromatography. The compounds of formula I may exist in the racemic form or as optically active isomers which are separated in the usual fashion. For example, the acids may be resolved by formation of salts with optically active bases.

The novel pharmacological compositions of the invention are comprised of at least one compound of formula I and an inert pharmaceutical carrier. The compositions may be in the form of tablets, dragées, gelules, granules, suppositories, injectable solutions or suspensions, pomades, creams, gels and aerosol preparations made in a known manner.

Examples of suitable excipients for the compositions are talc, arabic gum, lactose, starch, magnesium stearate, cacao butter, aqueous or non-aqueous vehicles, fatty bodies of animal or vegetable origin, paraffinic derivatives, glycols, preservatives and diverse wetting agents, emulsifiers or dispersants.

The compositions of the invention possess an antagonistic activity to prostaglandins as well as an antibiosynthesis action to prostaglandins. They are particularly endowed with analgesic, anti-inflammatory and smooth muscle relaxant properties. The compositions are therefore useful for the treatment of conditions caused by hypersecretion of prostaglandins or to prevent these conditions. They are also useful in the treatment of pain affecting smooth muscles, of acute or chronic pain, of inflammations of rhumatismic affections or of the skin and eyes (uveites) of hyperthemia expressed as a defense reaction. The compositions are also useful for the treatment of conditions resulting from hyperactivity of certain smooth muscles such as vascular conditions (diabetic retinopathy and cerebral constrictions), of bronchoconstrictions (asthma and allergies), intestinal hypermotility, dysmenorrhea, of abortion dangers and of premature delivery.

The novel method of the invention for relieving pain and inflammation in warm-blooded animals, including humans, comprises administering to warm-blooded animals an effective amount of at least one compound of formula I. The compounds may be administered orally, rectally, parenterally or locally by application to the skin or the mucous membranes and the usual useful dose is 0.4 to 40 mg/kg depending on the method of administrations.

The novel method of the invention for relaxing smooth muscles in warm-blooded animals comprises administering to warm-blooded animals an effective amount of at least one compound of formula I. The compounds may be administered orally, rectally, parenterally or locally by application to the skin or the mucous membranes and the usual useful dose is 0.4 to 40 mg/kg depending on the method of administrations.

The compounds of formula II wherein $R_3$ is alkyl of 1 to 4 carbon atoms are known and the higher esters may be prepared from these esters by transesterification with the appropriate alcohol.

In the following examples there are described several preferred embodiments to illustrate the invention. However, it should be understand that the invention is not intended to be limited to the specific embodiments.

EXAMPLE 1

Ethyl (1RS, 2RS, 5RS, 3'SR) (1'E) 2-hydroxy-5-(3'-hydroxy 1'-octenyl) cyclopentanecarboxylate and ethyl (1RS, 2SR, 5RS, 3'SR) (1'E) 2-hydroxy-5-(3'-hydroxy-1'-octenyl)-cyclopentanecarboxylate A mixture of 572 mg of ethyl 3-(3'-α-hydroxy-trans 1'-octenyl)-cyclopentanone-2-carboxylate, 23 ml of ethanol, 2.3 ml of water and 85 mg of sodium borohydride was stirred for 2 hours at 5° C and then a few drops of acetone were added. The mixture was then poured into a solution saturated with monosodium phosphate and the mixture was filtered. The filtrate was evaporated to dryness and the residue was taken up in ethyl acetate. The solution was washed with water, dried and evaporated to dryness to obtain 520 mg of a mixture of the 2α-OH and 2β-OH isomers. The latter was chromatographed over silica gel and was eluted with methylene chloride containing 2% methanol to obtain 203 mg of the 2α-isomer and 226 mg of the 2β-isomer of ethyl (1RS, 5RS, 3'SR) (1'E) 2-hydroxy-5-(3'-hydroxy-1'-octenyl)-cyclopentanecarboxylate.

| Analysis: | $C_{16}H_{28}O_4$ | |
|---|---|---|
| Calculated: | %C 67.6 | %H 9.85 |

| -continued | | |
|---|---|---|
| Found: | α: 67.6 β: 67.9 | α: 9.5 β: 9.5 |

EXAMPLE 2

Ethyl (1RS, 2RS, 5RS, 3'ξ) (1'E) 2,3'-dihydroxy-5-(3'-methyl-1'-octenyl)-cyclopentanecarboxylate STEP A: ethyl (1RS, 2RS, 5RS, 1'E) 2-hydroxy-5-(3'-oxo-1'-octenyl)-cyclopentanecarboxylate A mixture of 1 g of the β-isomer from Example 1, 20 ml of dioxane and 1.6 g of dichlorodicyanoquinone was stirred for 20 hours and was then filtered. The filtrate was poured into ice water and the mixture was extracted with methylene chloride. The organic extracts were washed with dilute sodium hydroxide, then with water and dried and evaporated to dryness. The residue was chromatographed over silica gel and eluted with a 1-1 cyclohexane-ethyl acetate mixture to obtain 940 mg of ethyl (1RS, 2RS, 5RS, 1'E) 2-hydroxy-5-(3'-oxo-1'-octenyl)-cyclopentanecarboxylate.

STEP B: ethyl (1RS, 2RS, 5RS, 3'ξ) (1'E) 2,3'-dihydroxy-5-(3'-methyl-1'-octenyl)-cyclopentanecarboxylate A solution of 850 mg of the product of Step A in 50 ml of tetrahydrofuran was cooled to 0° C and then 9.3 ml of 0.965 N methyl magnesium iodide in ether were added thereto. The mixture was stirred at 20° C for 20 hours and was then poured into ice water containing ammonium chloride. The mixture was extracted with methylene chloride and the organic extracts were washed with aqueous sodium chloride, dried and evaporated to dryness to obtain 873 mg of raw product. The latter was chromatographed over silica gel and was eluted with a cyclohexane-ethyl acetate mixture and a methylene chloride-ethyl acetate mixture to obtain 475 mg of ethyl (1RS, 2RS, 5RS, 3'ξ) (1'E), 2,3'-dihydroxy-5-(3'-methyl-1'-octenyl)-cyclopentanecarboxylate with an Rf = 0.22 (silica-1-1 cyclohexane-ethyl acetate mixture).

EXAMPLE 3

Nonyl (1RS, 2SR, 5RS, 3'-SR) (1'E) 2,3'-dihydroxy-5-(1'-octenyl)-cyclopentanecarboxylate A mixture of 200 mg of the 2α-isomer of Example 1, 4 ml of methanol, 1.5 ml of water and 1.4 ml of 1N sodium hydroxide solution was heated at 40°-45° C for an hour and the mixture was then evaporated to dryness. The residue was taken up in water and the solution was washed with ethyl acetate, acidified with 1N hydrochloric acid and extracted with ethyl acetate. The organic extracts were dried and evaporated to dryness to obtain 189 mg of raw (1RS, 2SR, 5RS, 3'SR) (1'E) 2,3'-dihydroxy-5-(1'octenyl)-cyclopentanecarboxylic acid.

A mixture of the said acid, 4 ml of methylene chloride, 0.5 ml of nonyl alcohol and 0.22 ml of triethylamine was stirred for 10 minutes and then 150 mg of p-toluene sulfonyl chloride were added thereto. The mixture was stirred for 1½ hours and was extracted with ethyl acetate. The organic extracts were washed with aqueous sodium chloride, dried and evaporated to dryness. The residue was chromatographed over silica gel and was eluted with methylene chloride containing 2% methanol to obtain 78 mg of nonyl (1RS, 2SR, 5RS, 3'SR) (1'E) 2,3'-dihydroxy-5-(1'-octenyl)-cyclopentanecarboxylate melting at 40° C.

EXAMPLE 4

Decyl (1RS, 2SR, 5RS, 3'SR) (1'E) 2,3'-dihydroxy-5-(1'-octenyl)-cyclopentanecarboxylate 166 mg of the sodium salt of (1RS, 2SR, 5RS, 3'SR) (1'E) 2,3'-dihydroxy-5-(1'-octenyl)-cyclopentanecarboxylic acid were reacted with decyl iodide in dimethylformamide to obtain 138 mg of decyl (1RS, 2SR, 5RS, 3'SR) (1'E) 2,3'-dihydroxy-5-(1'-octenyl)-cyclopentanecarboxylate melting at 37° C.

EXAMPLE 5

Ethyl (1RS, 2SR, 5RS, 3'ξ) (1'E) 2,3'-dihydroxy-5-(3'-methyl-1'-octenyl)-cyclopentanecarboxylate STEP A: ethyl (1RS, 2SR, 5RS, 1'E) 2-hydroxy-5-(3'-oxo-1'-octenyl)-cyclopentanecarboxylate Using the procedure of Step A of Example 2, 1 g of the 2α-isomer of Example 1 was reacted to obtain 930 mg of ethyl (1RS, 2SR, 5RS, 1'E) 2-hydroxy-5-(3'-oxo-1'-octenyl)-cyclopentanecarboxylate STEP B: ethyl (1RS, 2SR, 5RS, 3'ξ) (1'E) 2,3'-dihydroxy-5-(3'-methyl-1'-octenyl)-cyclopentanecarboxylate Using the procedure of Step B of Example 2, 700 mg of the product of Step A were reacted to obtain 390 mg of ethyl (1RS, 2SR, 5RS, 3'ξ) (1'E) 2,3'-dihydroxy-5-(3'-methyl-1'-octenyl)-cyclopentanecarboxylate with an Rf = 0.25 (silica gel — 85-15 methylene chloride-ethyl acetate mixture).

EXAMPLE 6

Ethyl (1RS, 2SR, 5RS, 3'SR) (1'E) 2-hydroxy-5-(3'-α-tetrahydropyranyloxy-1'-octenyl)-cyclopentanecarboxylate, ethyl (1RS, 2SR, 5RS, 3'SR) (1'E) 2-hydroxy-5-(3'-α-tetrahydropyranyloxy-1'-octenyl)-cyclopentanecarboxylate and ethyl (1SR, 2RS, 5RS, 3'SR) (1'E) 2-hydroxy-5-(3'α-tetrahydropyranyloxy-1'-octenyl)-cyclopentanecarboxylate A mixture of 14 g of ethyl 3-(3'α-tetrahydropyranyloxy-trans-1'-octenyl)-cyclopentanone-2-carboxylate, 200 ml of isopropanol, 20 ml of water and 5.6 g of sodium borohydride was stirred for 2 hours and acetone was slowly added thereto. The mixture was poured into water saturated with monosodium phosphate and the mixture was filtered. The filtrate was evaporated to dryness and the residue was taken up in ethyl acetate. The organic solution was washed with water, dried and evaporated to dryness. The residue was chromatographed over silica gel and was eluted with an 8-2 cyclohexane-ethyl acetate mixture containing 0.1% of triethylamine to obtain 3.4 g of the α-OH (2SR) isomer, 4 g of the β-OH (2RS) isomer and 570 mg of the β-OH (2RS),

isomer.

| Analysis: | $C_{21}H_{36}O_5$ | |
|---|---|---|
| Calculated: | %C 68.44 | %H 9.85 |
| Found: | α-OH 68.2 β-OH: 68.1 | α-OH: 9.6 β-OH: 9.7 |

EXAMPLE 7

Ethyl (1RS, 2SR, 5RS, 3'SR)
2-hydroxy-5-(3'-α-tetrahydropyranyloxy-1'-octyl)-cyclopentanecarboxylate A mixture of 513 mg of α-OH (2SR) isomer of Example 6, 12.5 ml of ethyl acetate and 150 mg of 10% palladized carbon was stirred under a hydrogen atmosphere until hydrogen absorption ceased and the mixture was filtered. The filtrate was evaporated to dryness and the residue was chromatographed over silica gel and was eluted with a 7-3 cyclohexane-ethyl acetate mixture containing 0.1% triethylamine to obtain 313 mg of ethyl (1RS, 2SR, 5RS, 3'SR) 2-hydroxy-5-(3'α-tetrahydropyranyloxy-1'-octyl)-cyclopentanecarboxylate with an Rf = 0.29 (silica gel — 7-3 cyclohexane-ethyl acetate mixture containing 0.1% triethylamine).

EXAMPLE 8

(1RS, 2SR, 5RS, 3'SR) (1'E)
2-hydroxy-5-(3'-α-tetrahydropyranyloxy-1'-octenyl)-cyclopentanecarboxylic acid A mixture of 3.1 g of the α-OH (2SR) isomer of Example 6, 50 ml of methanol and 8.15 ml of 2N sodium hydroxide was stirred for 3 hours at 20° C and the mixture was evaporated to dryness at 35°-40° C. The residue was taken up in water and the solution was washed with ethyl ether, was saturated with sodium chloride and acidified with hydrochloric acid. The mixture was extracted with ether and the ether extracts were washed with water, dried and evaporated to dryness to obtain 2.6 g of (1RS, 2SR, 5RS, 3'SR) (1'E) 2-hydroxy-5-(3'-α-tetrahydropyranyloxy-1'-octenyl)-cyclopentanecarboxylic acid.

| Analysis: | $C_{19}H_{32}O_5$ | |
|---|---|---|
| Calculated: | %C 67.03 | %H 9.47 |
| Found: | 66.8 | 9.5 |

EXAMPLE 9

Butyl (1RS, 2SR, 5RS, 3'SR) (1'E)
2-hydroxy-5-(3'-α-tetrahydropyranyloxy-1'-octenyl)-cyclopentanecarboxylate A solution of 59 mg of sodium bicarbonate in 1 ml of water was added to a solution of 240 mg of the acid of Example 8 in 1 ml of ethanol and the mixture was evaporated to dryness to form the sodium salt of the said acid. The latter was dissolved in 38 ml of dimethylformamide and after the addition of 0.8 ml of butyl iodide thereto, the mixture was stirred for 3 hours at 20° C. The mixture was evaporated to dryness and the residue was taken up in a water-ethyl acetate mixture. The mixture was decanted and the organic phase was dried and evaporated to dryness. The residue was chromatographed over silica gel and was eluted with a 75-25 cyclohexane-ethyl acetate mixture containing 0.1% of triethylamine to obtain 220 mg of butyl (1RS, 2SR, 5RS, 3'SR) (1'E) 2-hydroxy-5-(3'-α-tetrahydropyranyloxy-1'-octenyl)-cyclopentanecarboxylate with an Rf = 0.22 (silica gel — 75-25 cyclohexane-ethyl acetate mixture containing 0.1% of triethylamine).

EXAMPLE 10

Methyl (1RS, 2SR, 5RS, 3'SR) (1'E)
2-hydroxy-5-(3'-α-tetrahydropyranyloxy)-1'-octenyl)-cyclopentanecarboxylate A solution of diazomethane in methylene chloride was slowly added to a solution of 400 mg of the acid of Example 8 in 3 ml of methanol and the mixture was stirred for 10 minutes and then was evaporated to dryness. The residue was chromatographed over silica gel and was eluted with a 7-3 cyclohexane-ethyl acetate mixture containing 0.1% triethylamine to obtain 363 mg of methyl (1RS, 2SR, 5RS, 3'SR) (1'E) 2-hydroxy-5-(3'-α-tetrahydropyranyloxy-1'-octenyl)-cyclopentanecarboxylate with an Rf = 0.28 (silica gel 6-4 cyclohexane-ethyl acetate mixture containing 0.1% of triethylamine).

EXAMPLE 11

Propyl (1RS, 2SR, 5RS, 3'SR) (1'E)
2-hydroxy-5-(3'-α-tetrahydropyranyloxy-1'-octenyl)-cyclopentanecarboxylate Using the procedure of Example 9, 703 mg of the sodium salt of the acid of Example 8 and a solution of n-propyl iodide in dimethylformamide were reacted to obtain 434 mg of propyl (1RS, 2SR, 5RS, 3'SR) (1'E) 2-hydroxy-5-(3'-α-tetrahydropyranyloxy-1'-octenyl)-cyclopentanecarboxylate with an Rf = 0.45 (silica gel — 6-4 cyclohexane-ethyl acetate mixture containing 0.1% of triethylamine.

EXAMPLE 12

Ethyl (1RS, 2RS, 5RS, 3'SR)
2-hydroxy-5-(3'α-tetrahydropyranyloxy-1'-octyl)-cyclopentanecarboxylate Using the procedure of Example 7, 500 mg of the β-OH (1RS) isomer of Example 6 were reacted to obtain 191 mg of ethyl (1RS, 2RS, 5RS, 3'SR) 2-hydroxy-5-(3'-α-tetrahydropyranyloxy-1'-octyl)-cyclopentanecarboxylate with an Rf = 0.25 (silica gel 7-3 cyclohexane-ethyl acetate mixture containing 0.1% of triethylamin.

EXAMPLE 13

(1RS, 2RS, 5RS, 3'SR) (1'E)
2-hydroxy-5-(3'-α-tetrahydropyranyloxy-1'-octenyl)-cyclopentanecarboxylic acid Using the procedure of Exampel 8, 3.5 g of the β-OH (1RS) isomer of Example 6 were reacted to obtain 3.1 g of (1RS, 2RS, 5RS, 3'SR) (1'E) 2-hydroxy-5-(3'-α-tetrahydropyranyloxy-1'-octenyl)-cyclopentanecarboxylic acid

| Analysis: | $C_{19}H_{32}O_5$ | |
|---|---|---|
| Calculated: | %C 67.03 | %H 9.47 |
| Found: | 66.8 | 9.4 |

EXAMPLE 14

Methyl (1RS, 2RS, 5RS, 3'SR) (1'E)
2-hydroxy-5-(3'-α-tetrahydropyranyloxy-1'-octenyl)-cyclopentanecarboxylate Using the procedure of Example 10, 0.85 g of the free acid of Example 13 were reacted to obtain 0.8 g of methyl (1RS, 2RS, 5RS, 3'SR) (1'E) 2-hydroxy-5-(3'-α-tetrahydropyranyloxy-1'-octenyl)-cyclopentanecarboxylate with a Rf = 0.25 (silica gel — 6-4 cyclohexane-ethyl acetate mixture containing 0.1% of triethylamine).

EXAMPLE 15

Propyl (1RS, 2RS, 5RS, 3'SR) (1'E) 2-hydroxy-5-(3'-α-tetrahydropyranyloxy-1'-octenyl)-cyclopentanecarboxylate Using the procedure of Example 11, 457 ml of the sodium salt of the acid of Example 13 and propyl iodide were reacted to obtain 392 mg of propyl (1RS, 2RS, 5RS, 3'SR) (1'E) 2-hydroxy-5-(3'-α-tetrahydropyranyloxy-1'-octenyl)-cyclopentanecarboxylate with an Rf = 0.32 (silica gel — 6-4 cyclohexane-ethyl acetate mixture containing 0.1% of triethylamine).

EXAMPLE 16

Ethyl (1RS, 2SR, 5RS, 3'SR) (1'E) 2-hydroxy-5-(3'-hydroxy-3'-ethynyl-1'-octenyl)-cyclopentanecarboxylate

STEP A: ethyl (5RS, 3'SR, 1'E) 2-methoxy-5-(3'-hydroxy-1'-octenyl)-1-cyclopentenecarboxylate 300 ml of a methylene chloride solution of 15 g/liter of diazomethane were added at 0° C to a solution of 7.01 g of ethyl 3-(3'-hydroxy-trans-1'-octenyl)-cyclopentanone-2-carboxylate in 100 ml of methylene chloride and the mixture was stirred for 4 hours at 20° C and then was evaporated to dryness. The residue was chromatographed over silica gel and was eluted with a 4-6 cyclohexane-ethyl acetate mixture containing 0.01% of triethylamine to obtain 6.3 g of ethyl (5RS, 3'SR, 1'E) 2-methoxy-5-(3'-hydroxy-1'-octenyl)-1-cyclopentenecarboxylate.

STEP B: ethyl (5RS, 1'E) 2-methoxy-5-(3'-oxo-1'-octenyl)-1-cyclopentenecarboxylate A mixture of 100 mg of the product of Step A, 15 ml of benzene and 211 mg of 93% silica silicate was refluxed for an hour and was then filtered. The filtrate was evaporated to dryness and the residue was chromatographed over silica gel and was eluted with an 8-2 benzene-ethyl acetate mixture containing 0.5% of triethylamine to obtain 70 mg of ethyl (5RS, 1'E) 2-methoxy-5-(3'-oxo-1'-octenyl)-1-cyclopentenecarboxylate with an Rf = 0.2 (silica gel — 8-2 benzene-ethyl acetate mixture containing 0.5% of triethylamine).

STEP C: ethyl (5RS, 3'RS, 1'E) 2-methoxy-5-(3'-hydroxy-3'-ethynyl-1'-octenyl)-cyclopentanecarboxylate and ethyl (5RS, 3'SR, 1'E) 2-methoxy-5-(3'-hydroxy-3'-ethynyl-1'-octenyl)-1-cyclopentene-carboxylate 3.3 ml of a solution of 0.9 M of ethynyl magnesium bromide obtained from the reaction of ethyl magnesium bromide and acetylene in tetrahydrofuran were added at −10° C to a solution of 660 mg of the product of Step B in 10 ml of tetrahydrofuran and the mixture was stirred at −5° C until disappearance of the starting material. The mixture was poured into an aqueous solution saturated with ammonium chloride and the mixture was extracted with ether. The organic extracts were dried and evaporated to dryness and the residue was chromatographed over silica gel. Elution with a 9-1 methylene chloride-ethyl acetate mixture containing 0.5% of triethylamine yielded 144 mg of the β-OH isomer with a Rf = 0.26 and 216 mg of the α-OH isomer with an Rf = 0.23 with the above eluant.

STEP D: ethyl (1RS, 5RS, 3'SR, 1'E) 2-oxo-5-(3'-hydroxy-3'-ethynyl-1'-octenyl)-cyclopentanecarboxylate A mixture of 1.135 g of the α-OH isomer of Step C, 35 ml of ethanol, 3.5 ml of water and 0.87 ml of 1N hydrochloric acid was stirred at 20° C for 70 hours and was then poured into water. The mixture was extracted with ethyl acetate and the organic phase was washed with water, dried and evaporated to dryness. The residue was chromatographed over silica gel and was eluted with an 8-2 benzene-ethyl acetate mixture to obtain 846 mg of ethyl (1RS, 2RS, 3'SR, 1'E) 2-oxo-5-(3'-hydroxy-3'-ethynyl-1'-octenyl)-cyclopentanecarboxylate with an Rf = 0.33 with the above eluant.

STEP E: ethyl (1RS, 2SR, 5RS, 3'SR) (1'E) 2-hydroxy-5-(3'-hydroxy-3'-ethynyl-1'-octenyl)-cyclopentanecarboxylate A mixture of 390 mg of the product of Step D, 10 ml of ethanol, 1 ml of water and 53 mg of sodium borohydride was stirred at 5° C for 2 hours and was then poured into water. The mixture was extracted with methylene chloride and the organic phase was washed with water, dried and evaporated to dryness. The residue was chromatographed over silica gel and was eluted with a 8-2 benzene-ethyl acetate mixture to obtain 180 mg of ethyl (1RS, 2SR, 5RS, 3'SR) (1'E) 2-hydroxy-5-(3'-hydroxy-3'-ethynyl-1'-octenyl)-cyclopentanecarboxylate with an Rf = 0.13 with the above eluant.

EXAMPLE 17

Ethyl (1RS, 2SR, 5RS, 3'SR) (1'E) 2-hydroxy-5-(3'-α-tetrahydropyranyloxy-3'-ethynyl-1'-octenyl)-cyclopentanecarboxylate and ethyl (1RS, 2RS, 5RS, 3'SR) (1'E)2-hydroxy-5-(3'-α-tetrahydropyranyloxy-3'-ethynyl-1'-octenyl)-cyclopentanecarboxylate

STEP A: ethyl (1RS, 5RS, 3'SR, 1'E) 2-oxo-5-(3'-α-tetrahydropyranyloxy-3'-ethynyl-1'-octenyl)-cyclopentanecarboxylate A mixture of 840 mg of the product of Step D in Example 16, 17 ml of ether, 0.84 ml of dihydropyran and 8.4 mg of p-toluene sulfonic acid was stirred at 20° C for 16 hours and a few drops of pyridine were added thereto. The mixture was poured into water and the mixture was extracted with petroleum ether. The organic extracts were washed with sodium bicarbonate solution and water, dried and evaporated to dryness. The residue was chromatographed over silica gel and was eluted with a 75-25 cyclohexane-ethyl acetate mixture containing 0.1% of triethylamine to obtain 1.05 g of product which was chromatographed a second time to separate the two isomers which resulted in 545 mg of isomer A with an Rf = 0.3 and 433 mg of isomer B with an Rf = 0.22.

STEP B: ethyl (1RS, 2SR, 5RS, 3'SR)(1'E) 2-hydroxy-5-(3'-α-tetrahydropyranyloxy-3'-ethynyl-1'-octenyl)-cyclopentanecarboxylate and ethyl (1RS, 2RS, 5RS, 3'SR)(1'E) 2-hydroxy-5-(3'-α-tetrahydropyrayloxy-3'-ethynyl-1'-octenyl)-cyclopentanecarboxylate 56 mg of sodium bicarbonate were added at 0 to −5° C to a mixture of 545 mg of the product of Step A, 13.9 ml of ethanol and 1.4 ml of water and the mixture was stirred for an hour and was then poured into an aqueous monosodium phosphate solution. The mixture was extracted with methylene chloride and the extracts were washed with water, dried and evaporated to dryness. The residue was chromatographed over silica gel and was eluted with an 8-2 benzene-ethyl acetate mixture containing 0.1% of triethylamine to obtain 205 mg of the α-OH isomer and 167 mg of β-OH isomer of ethyl (1RS, 2RS and 2SR, 5RS, 3'SR, 1'E) 2-hydroxy-5-(3'-α-tetrahydropyranyloxy-3'-ethynyl-1'-octenyl)-cyclopentanecarboxylate with an Rf = 0.4 and 0.35, respectively, with the above eluant.

EXAMPLE 18

Ethyl (1RS, 2RS, 5RS, 3'RS) (1'E) 2-hydroxy-5-(3'-ethynyl-3'-α-tetrahydropyranyloxy-1'-octenyl)-cyclopentanecarboxylate and ethyl (1RS, 2SR, 5RS, 3'RS) (1'E) 2-hydroxy-5-(3'-ethynyl-3'-α-tetrahydropyranyloxy-1'-octenyl)-cyclopentanecarboxylate

STEP A: ethyl (1RS, 5RS, 3'RS, 1'E) 2-oxo-5-(3'-hydroxy-3'-ethynyl-1'-octenyl)-cyclopentanecarboxylate Using the procedure of Step D of Example 16, 130 mg of the β-OH, 3'RS isomer of Step C of Example 16 were reacted to obtain 70 mg of ethyl (1RS, 5RS, 3'RS, 1'E) 2oxo-5-(3'-hydroxy-3'-ethynyl-1'-octenyl)-cyclopentanecarboxylate with an Rf = 0.4 (silica gel — 8-2 benzene-ethyl acetate mixture).

| Analysis: | $C_{18}H_{26}O_4$ | |
|---|---|---|
| Calculated: | %C 70.56 | %H 8.55 |
| Found: | 70.3 | 8.4 |

STEP B: ethyl (1RS, 5RS, 3'RS) (1'E) 2-oxo-5-(3'-ethynyl-3'-α-tetrahydropyranyloxy-1'-octenyl)-cyclopentanecarboxylate Using the procedure of Step A of Example 17, 258 mg of the product of Step A were reacted to obtain 306 mg of ethyl (1RS, 5RS, 3'RS, 1'E) 2-oxo-5-(3'-ethynyl-3'-α-tetrahydropyranyloxy-1'-octenyl)-cyclopentanecarboxylate with an Rf = 0.32 (silica gel — 7-3 cyclohexane-ethyl acetate mixture containing 0.1% of triethylamine).

STEP C: ethyl (1RS, 2RS, 5RS, 3'RS) (1'E) 2-hydroxy-5-(3'-ethynyl-3'-α-tetrahydropyranyloxy-1'-octenyl)-cyclopentanecarboxylate and ethyl (1RS, 2SR, 5RS, 3'RS) (1'E) 2-hydroxy-5-(3'-ethynyl-3'-α-tetrahydropyranyloxy-1'-octenyl)-cyclopentanecarboxylate Using the procedure of step B of Example 17, 280 mg of the product of Step B were reacted to obtain 55 mg of the above α-OH isomer and 27 mg of the above β-OH isomer with an Rf = 0.25 and 0.21, respectively (silica gel — 7-3 cyclohexaneethyl acetate mixture containing 0.1% of triethylamine).

EXAMPLE 19

(1RS, 2RS, 3RS, 3"SR) (1"E) 2-(1'-butanon-1'-yl)-3-(3"-α-tetrahydropyranyloxy-1"-octenyl)-cyclopentanol A mixture of 260 mg of the product of Example 13, 13 ml of ether and 1.97 ml of a solution of 1.2 M of propyllithium in ether was stirred at 0° C for 30 minutes and was then poured into a mixture of ice, water, ethyl acetate and monosodium phosphate. The mixture was decanted and the aqueous phase was extracted with ethyl acetate. The organic extracts were dried and evaporated to dryness and the residue was chromatographed over silica gel. Elution with an 8-2 cyclohexane-ethyl acetate mixture yielded 126 mg of (1RS, 2RS, 3RS, 3"SR) (1"E) 2-(1'butanon-1'-yl)-3-(3"-α-tetrahydropyranyloxy-1"-octenyl)-cyclopentanol with an Rf = 0.2 (eluant as above).

EXAMPLE 20

(1SR, 2RS, 3RS, 3"SR) (1"E) 2'-(1'-butanon-1'-yl)-3-(3"-α-tetrahydropyranyloxy-1"-octenyl)-cyclopentanol Using the procedure of Example 19, 230 mg of the product of Example 8 and 1.68 ml of a solution of 1.25 M propyllithium in ether were reacted to obtain 102 mg of (1SR, 2RS, 3RS, 3"SR) (1"E) 2-(1'-butanon-1'-yl)-3-(3"-α-tetrahydropyranyloxy-1"-octenyl)-cyclopentanol with an Rf = 0.27 (silica gel — 7-3 cyclohexane-ethyl acetate mixture).

PHARMACOLOGICAL STUDY

The following compounds were used in the pharmacological tests reported herein:

| Product | Compound |
|---|---|
| A | ethyl (1RS, 2RS, 5RS, 3'-SR) (1'E) 2-hydroxy-5-(3'-hydroxy-1'-octenyl)-cyclopentanecarboxylate |
| B | ethyl (1RS, 2SR, 5RS, 3'SR) (1'E) 2-hydroxy-5-(3'-hydroxy-1'-octenyl)-cyclopentanecarboxylate |
| C | ethyl (1RS, 2RS, 5RS, 3'ξ) (1'E) 2,3'-dihydroxy-5-(3'-methyl-1'-octenyl)-cyclopentanecarboxylate |
| D | nonyl (1RS, 2SR, 5RS, 3'SR) (1'D) 2,3'-dihydroxy-5-(1'-octenyl)-cyclopentanecarboxylate |
| E | ethyl (1RS, 2SR, 5RS, 3'ξ) (1'E) 2,3'-dihydroxy-5-(3'-methyl-1'-octenyl)-cyclopentanecarboxylate |
| F | ethyl (1RS, 2SR, 5RS, 3'SR) (1'E) 2-hydroxy-5-(3'-α-tetrahydropyranyloxy-1'-octenyl)-cyclopentanecarboxylate |
| G | ethyl (1RS, 2RS, 5RS, 3'SR) (1'E) 2-hydroxy-5-(3'-α-tetrahydropyranyloxy-1'-octenyl)-cyclopentanecarboxylate |
| H | ethyl (1RS, 2SR, 5RS, 3'SR) 2-hydroxy-5-(3'-α-tetrahydropyranyloxy-1'-octyl)-cyclopentanecarboxylate |
| I | methyl (1RS, 2SR, 5RS, 3'SR) (1'E) 2-hydroxy-5-(3'-α-tetrahydropyranyloxy-1'-octenyl)-cyclopentanecarboxylate |
| J | propyl (1RS, 2SR, 5RS, 3'SR) (1'E) 2-hydroxy-5-(3'-α-tetrahydropyranyloxy-1'-octenyl)-cyclopentanecarboxylate |
| K | ethyl (1RS, 2SR, 5RS, 3'SR) 2-hydroxy-5-(3'-α-tetrahydropyranyloxy-1'-octyl)-cyclopentanecarboxylate |
| L | methyl (1RS, 2RS, 5RS, 3'SR) (1'E) 2-hydroxy-5-(3'-α-tetrahydropyranyloxy-1'-octenyl)-cyclopentanecarboxylate |
| M | propyl (1RS, 2RS, 5RS, 3'SR) (1'E) 2-hydroxy-5-(3'-α-tetrahydropyranyloxy-1'-octenyl)-cyclopentanecarboxylate |
| N | ethyl (1RS, 2SR, 5RS, 3'SR) (1'E) 2-hydroxy |

| Product | Compound |
|---|---|
| | -5-(3'-hydroxy-3'-ethynyl-1'-octenyl)-cyclopentanecarboxylate |
| O | ethyl (1RS, 2SR, 5RS, 3'SR) (1'E) 2-hydroxy-5-(3'-ethynyl-3'-α-tetrahydropyranyloxy-1'-octenyl)-cyclopentanecarboxylate |
| P | ethyl (1RS, 2RS, 5RS, 3'SR) (1'E) 2-hydroxy-5-(3'-ethynyl-3'-α-tetrahydropyranyloxy-1'-octenyl)-cyclopentanecarboxylate |
| Q | (1RS, 2RS, 3RS, 3"SR) (1"E) 2-(1'-butanon-1'-yl)-3-(3"-α-tetrahydropyranyloxy-1"-octenyl)-cyclopentanol |
| R | ethyl (1SR, 2RS, 5RS, 3'SR) (1'E) 2-hydroxy-5-(3'-α-tetrahydropyranyloxy-1'-octenyl)-cyclopentanecarboxylate |
| S | (1SR, 2RS, 3RS, 3"SR) (1"E) 2-(1'butanon-1'-yl)-3-(3"-α-tetrahydropyranyloxy-1"-octenyl)-cyclopentanol |

A. Antagonistic activity to the contracturant effect of prostaglandin E₂

The antagonistic effect of the test compounds to the contracturant activity of prostaglandin $E_2$ was determined by the method of Magnus wherein a portion of the colon adjacent to the caecum was removed from a rat and was washed with a Krebs solution at 37° C. The colon was then suspended in a bath of oxygenated Krebs liquid kept at 37° C and the contactions of the organ were registered with a collector attached to a Sanborn polygraph. The organ was first standarized with prostaglandin $E_2$ to determine the concentration necessary to obtain a significant contraction (5 to 10 ng/ml). The antagonistic product was added to the bath 30 seconds before the standard dose of $PGE_2$ and the intensity of the contraction was measured. The concentration of product which inhibited by 50% the contractions provoked by $PGE_2$ was determined by the straight line effect-log of the dose and the $CI_{50}$ is reported in Table I.

TABLE I

| Product | $CI_{50}$ in μg/ml against $PGE_2$ |
|---|---|
| A | 20 |
| F | 20 |
| G | 20 |

B. Relaxant Activity on the guinea pig ileon

The relaxant effect of the test compounds was determined on guinea pig ileon using the procedure of Test A above. The terminal portion of the guinea pig ileon was removed and washed with Tyrode solution at 37° C. It was then suspended in an bath of oxygenated Tyrode liquid at 37° C and the contractions were registered on a collector attached to a Sanborn polygraph. The test product was added to bath of the organ with a low volume and the concentration which caused a suppression of spontaneous contractions and relaxed the organ, cuasing a lowering of the line of the base was considered to be relaxant. The results are reported in Table II.

TABLE II

| Product | Relaxant action in μg/ml | Product | Relaxant action in μg/ml |
|---|---|---|---|
| A | 20 | J | 10 |
| B | 20 | K | 5 |
| C | 1 | L | 5 |
| D | 10 | M | 5 |
| E | 5 | N | 5 |
| F | 20 | O | 10 |
| G | 20 | P | 5 |
| H | 10 | Q | 10 |
| I | 5 | | |

C. Analgesic Activity — stretching provoked by acetic acid

The test procedure was that of Koster et al wherein an interitoneal injection of aqueous acetic acid in a concentration of 1% at a dose of 100 mg/kg caused in mice repeated movements of strectching and twisting which can persist for more than 6 hours. Analgesics prevent or lessen the syndrome. The test products were orally administered one half hour before the acetic acid injection and the mice were fasted from the day before the tests. The stretching were counted for each mouse during a 15 minute observation period beginning right after the acetic acid injection and the analgesic affect was expressed as a percentage of protection with respect to the controls. The $DA_{50}$ dose which reduced the number of stretchings by 50% was determined and is reported in Table III.

TABLE III

| Product | $DA_{50}$ in mg/kg |
|---|---|
| B | 100 |
| F | ~100 |
| G | ~100 |
| P | ~100 |

D. Inhibitory effect against biosynthesis of prostaglandins

Synthesis of prostaglandins starting with arachidonic acid by means of prostaglandin synthetases of lungs of guinea pigs This test used the procedure of Vane [Nature New-Biology, Vo. 231 (1971), p. 232–235] wherein the lungs of adult guinea pigs (two per series) were rapidly removed and washed with a modified, iced Bucher medium. The lung tissue was homogenized in a Turrax grinder in a minute and the homogenate was centrifuged for 20 minutes to 1200 g. The supernatant was used as a preparation of prostaglandin synthetases.

A solution of arachidonic acid in ethanol at a concentration of 10 mg/ml was diluted with a 0.2% aqueous sodium carbonate solution and was then diluted further with a modified Bucher medium to obtain a final acid concentration of 200 μg/ml. The biosynthesis inhibitors are put into aqueous on dilute alcohol (20% maximum) solutions. Tubes were prepared containing 1 ml of the prostaglandin synthetases preparation, 10 μg of arachidonic acid and 0.1 ml of inhibiting solution or, for the controls, an equal volume of water or dilute alcohol. The tubes were incubated with stirring for 30 minutes at 37° C in aerobic conditions and each test consisted of a tube containing a biosynthesis inhibitor, one biosynthesis control with incubated arachidonic acid and one control with non-incubated arachidonic acid. The latter control permitted a evaluation of amount of natural prostaglandins present in the ground lung and the results obtained with this control must therefore be taken away from the control of biosynthesis and from all the tests. The reactions are stopped by immersion in boiling water until the proteins are coagulated. The dosage of "prostaglandin like" activity was effected biologically on the isolated rat colon suspended in Krebs liquid, mixed to augment the specificity, with antagonists to other contracturant mediators susceptible to interfere. The antagonists were mepyramine, scopolamine, methysergide, phenoxybenzamine and propanolol.

A comparison of the results registered in the presence or absence of a test product permitted the calculation of the percentage of biosynthesis inhibition. The $CI_{50}$ dose which inhibited by 50% the biosynthesis activity was graphically obtained by straight line representing the percent of inhibition with reference to the incubated controls against the log of the concentration in μg/ml and the results are reported in Table IV.

TABLE IV

| Product | $CI_{50}$ in $10^{-4}$ M |
|---|---|
| M | 6.52 |
| R | 5.42 |
| F | 0.54 |
| G | 2.04 |
| S | 6.28 |
| B | 3.76 |
| C | 5.03 |
| D | 5.23 |
| E | 6.04 |
| P | 3.82 |
| O | 2.29 |

Various modifications of the products and processes of the invention may be made without departing from the spirit or scope thereof and it is to be understood that the invention is to be limited only as defined in the appended claims.

We claim:
1. A compound of the formula

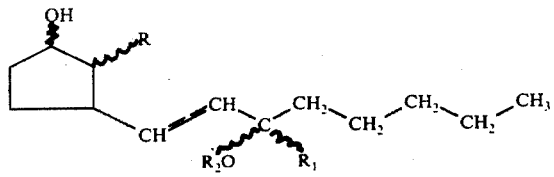

wherein R is selected from the group consisting of

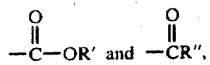

R' is selected from the group consisting of hydrogen, alkyl of 1 to 12 carbon atoms and a non-toxic, pharmaceutically acceptable cation, R" is alkyl of 1 to 6 carbon atoms, $R_1$ is selected from the group consisting of hydrogen and straight or branched chain, saturated and unsaturated alkyl of 1 to 4 carbon atoms and $R_2$ is selected from the group consisting of hydrogen and tetrahydropyranyl, the wavy lines connecting R and —OH to the cyclopentane ring and —$OR_2$ and $R_1$ to the chain indicates that the substituents may be in either of the possible positions on the carbon atoms to which they are attached and the dotted line indicates the optional presence of a double bond.

2. A compound of claim 1 wherein R is selected from the group consisting of

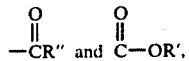

R" is alkyl of 1 to 3 carbon atoms, R' is selected from the group consisting of hydrogen, alkali metal cation and alkyl of 1 to 10 carbon atoms and $R_1$ is selected from the group consisting of hydrogen, methyl and ethynyl.

3. A compound of claim 1 wherein R is

R' is alkyl of 1 to 3 carbon atoms and $R_1$ is selected from the group consisting of hydrogen, methyl and ethynyl.

4. A compound of claim 1 which is ethyl (1RS, 2RS, 5RS, 3'ξ) (1'E) 2,3'-dihydroxy-5-(3'-methyl-1'-octenyl)-cyclopentanecarboxylate.

5. A compound of claim 1 which is ethyl (1RS, 2SR, 5RS, 3'ξ) (1'E) 2,3'-dihydroxy-5-(3'-methyl-1'-octenyl)-cyclopentanecarboxylate.

6. A compound of claim 1 which is methyl (1RS, 2SR, 5RS, 3'SR) (1'E) 2-hydroxy-5-(3'α-tetrahydropyranyloxy-1'-octenyl)-cyclopentanecarboxylate.

7. A compound of claim 1 which is ethyl (1RS, 2RS, 5RS, 3'SR) (1'E) 2-hydroxy-5-(3'-hydroxy-1'-octenyl)-cyclopentanecarboxylate.

8. A compound of claim 1 which is ethyl (1RS, 2SR, 5RS, 3'SR) (1'E) 2-hydroxy-5-(3'-α-tetrahydropyranyloxy-1'-octenyl)-cyclopentanecarboxylate.

9. A compound of claim 1 which is ethyl (1RS, 2RS, 5RS, 3'SR) (1'E) 2-hydroxy-5-(3'-α-tetrahydropyranyloxy-1'-octenyl)-cyclopentanecarboxylate.

10. A compound of claim 1 which is ethyl (1RS, 2SR, 5RS, 3'SR) (1'E) 2-hydroxy-5-(3'-hydroxy-3'-ethynyl-1'-octenyl)-cyclopentanecarboxylate.

11. A compound of claim 1 which is ethyl (1RS, 2RS, 5RS, 3'SR) (1'E) 2-hydroxy-5-(3'-α-tetrahydropyranyloxy-3'-ethynyl-1'-octenyl)-cyclopentanecarboxylate.

12. An analgesic and anti-inflammatory composition comprising an analgesically effective amount of at least one compound of claim 1 and an inert pharmaceutical carrier.

13. A method of relieving pain and inflammation in warm-blooded animals comprising administering to warm-blooded animals an analgesically effective amount of at least one compound of claim 1.

14. The method of claim 13 wherein R is selected from the group consisting of

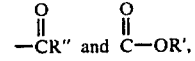

R" is alkyl of 1 to 3 carbon atoms, R' is selected from the group consisting of hydrogen, alkali metal cation and alkyl of 1 to 10 carbon atoms and $R_1$ is selected from the group consisting of hydrogen, methyl and ethynyl.

15. The method of claim 13 wherein the compound is ethyl (1RS, 2SR, 5RS, 3'SR) (1'E) 2-hydroxy-5-(3'-α-tetrahydropyranyloxy-1'-octenyl)-cyclopentanecarboxylate.

16. A composition for relaxing smooth muscles comprising a smooth muscle relaxant effective amount of at least one compound of claim 1 and an inert pharmaceutical carrier.

17. A method of relaxing smooth muscles in warm-blooded animals comprising administering to warm-blooded animals a smooth muscle relaxant effective amount of at least one compound of claim 1.

18. The method of claim 17 wherein R is selected from the group consisting of $$-\overset{O}{\underset{\|}{C}}R'' \text{ and } \overset{O}{\underset{\|}{C}}-OR',$$

R" is alkyl of 1 to 3 carbon atoms, R' is selected from the group consisting of hydrogen, alkali metal cation and alkyl of 1 to 10 carbon atoms and $R_1$ is selected from the group consisting of hydrogen, methyl and ethynyl.

19. The method of claim 17 wherein the compound is ethyl (1RS, 2SR, 5RS, 3'SR) (1'E) 2-hydroxy-5-(3'-α-tetrahydropyranyloxy-1'-octenyl)-cyclopentanecarboxylate.

* * * * *